United States Patent [19]

Mayer et al.

[11] Patent Number: 5,159,829

[45] Date of Patent: * Nov. 3, 1992

[54] DEVICE FOR MEASURING GAS PERMEATION

[75] Inventors: Daniel W. Mayer, St. Paul; Robert L. Neiss, St. Michael, both of Minn.

[73] Assignee: Modern Controls, Inc., Minneapolis, Minn.

[*] Notice: The portion of the term of this patent subsequent to Apr. 28, 2009 has been disclaimed.

[21] Appl. No.: 822,366

[22] Filed: Jan. 17, 1992

Related U.S. Application Data

[63] Continuation of Ser. No. 630,161, Dec. 19, 1990, Pat. No. 5,107,696.

[51] Int. Cl.[5] .................. G01N 15/08; G01M 3/00
[52] U.S. Cl. ............................................ 73/38
[58] Field of Search ................. 73/38, 64.3, 37

[56] References Cited

U.S. PATENT DOCUMENTS

| | | | |
|---|---|---|---|
| 3,498,110 | 7/1967 | Brun | 73/38 |
| 3,590,634 | 7/1971 | Pasternak et al. | 73/157 |
| 3,618,361 | 3/1970 | Stephens et al. | 73/38 |
| 4,464,927 | 8/1984 | Reid | 73/38 |
| 4,468,951 | 9/1984 | Garcia et al. | 73/38 |
| 4,586,376 | 5/1986 | Ortmans | 73/38 |
| 4,660,411 | 4/1987 | Reid | 73/38 |
| 4,663,969 | 5/1987 | Bibby et al. | 73/38 |
| 4,852,389 | 8/1989 | Mayer | 73/38 |

Primary Examiner—Hezron E. Williams
Assistant Examiner—Howard Wisnia
Attorney, Agent, or Firm—Palmatier & Sjoquist

[57] ABSTRACT

A system for measuring gas permeability of membranes under precise temperature and humidity controls, by the use of a gas detector made from a single metallic block, wherein the gas flow passages are virtually entirely confined within the metallic block, and a temperature control passage is provided in the block for stabilizing temperature of the block and the passages therein, at any predetermined temperature. The detector device also includes passages for forming into liquid reservoirs, for providing a controllable relative humidity by passing the test gases through the mubidifier passages.

11 Claims, 6 Drawing Sheets

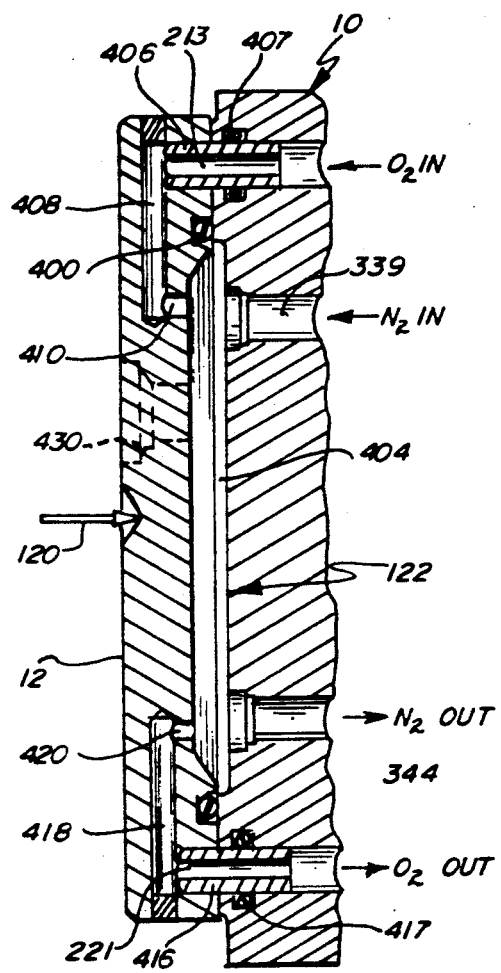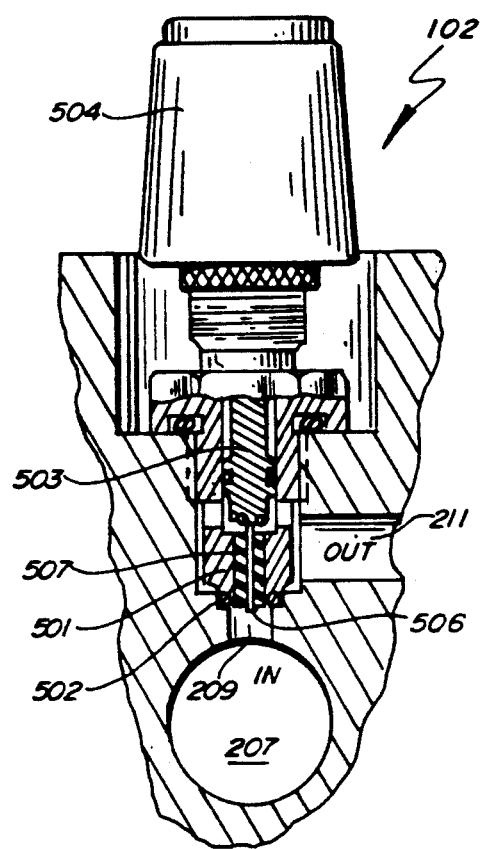

DEVICE FOR MEASURING GAS PERMEATION

This is a continuation of application Ser. No. 07/630,161, filed Dec. 19, 1990, now U.S. Pat. No. 5,107,696, issued Apr. 28, 1992.

BACKGROUND OF THE INVENTION

The present invention relates to a device for measuring gas permeability through a membrane; more particularly, the invention is an improved gas permeability measuring device which permits such measurements to be accomplished at substantially constant temperature and relative humidity.

Gas permeability measuring devices are generally known in the prior art, including a number of such devices which are manufactured by the assignee of the present invention. Such devices typically include one or more sensing heads which are adapted for holding a membrane material across a chamber, wherein a gas such as oxygen may be admitted into the chamber on one side of the membrane, and a detector such as an oxygen detector may be coupled via passages to the other side of the chamber, to measure the amount of oxygen which passes through the membrane. Since all membranes are permeable to some extent, it is usually possible to detect a measurable amount of oxygen passing through the membrane over a finite period of time. In the prior art, gas permeability measuring devices utilized one or more of such measuring heads coupled via hoses and tubing to sensors and the like, to perform fairly accurate measurements of membrane permeability.

Measurement of gas permeability through membranes requires extremely sensitive gas detectors or sensors, for the quantities of measured gas are frequently quite low. It is therefore extremely important that the entire system involved in such measurements be maintained under tightly sealed conditions, particularly with respect to all of the gas flow passages leading to the gas detector. Prior art permeability measuring instruments typically utilize hoses or tubing to interconnect the necessary instrumentation, wherein each of the connecting junctions is susceptible to leakage. Since the performance of these instruments can be critically degraded by gas leakage, it is important to the design of such instruments to provide a minimum number of connections in the gas flow path.

It is also known in the prior art to construct gas permeability sensors operating under various conditions of relative humidity of the gas. Relative humidity becomes an important factor in measuring gas permeability through membranes, because the permeability of certain membranes is affected by the relative humidity of the membrane and the surrounding gas. Measuring gas permeability under conditions of high relative humidity is exceedingly difficult to accomplish, because relative humidity and temperature are closely interrelated, and it therefore becomes necessary to maintain precise control over temperature if permeability is to be measured under relatively high humidity conditions. Under these conditions it is necessary to control temperature of all of the gas flow paths in the system, for a 1° C. change in temperature can easily result in a 5% change in relative humidity. Furthermore, under high relative humidity conditions a slight decrease in temperature can cause immediate condensation of the gas, resulting in liquid accumulation in the gas flow passages. Therefore it becomes extremely important to control the temperature of the entire measurement system whenever permeability measurements are desired with respect to humid gases.

Among the systems devised in the prior art for measuring permeability are a line of products manufactured by the assignee of the present invention under the general model designation "OX-TRAN." These systems have proved very effective for measuring gas permeability under widely varying conditions, although permeability measurement under high humidity conditions have necessitated relatively expensive and complex improvements to the basic system models. Examples of patented prior art technology can be found in U.S. Pat. No. 3,590,634 "Instrument for Determining Permeation Rates Through a Membrane," which describes a simple permeation measuring device utilizing dry gases. U.S. Pat. No. 4,464,927 "Apparatus for Measuring Gas Transmission Through Films," Aug. 14, 1984, describes another simple measuring device utilizing multiple permeation cells. U.S. Pat. No. 4,852,389 "System for Controlled Humidity Tests," Aug. 1, 1989, discloses a gas permeability measuring device capable of operating under different conditions of relative humidity in the gas. This last patent illustrates the complexity of equipment which has been necessary in order to accurately accomplish permeability measurements under conditions of controlled humidity and temperature.

SUMMARY OF THE INVENTION

The present invention comprises a gas permeability measuring device wherein humidity and temperature may be precisely controlled, by the expedient and novel construction of incorporating all of the gaseous passages into a single metallic block, and by including in the single metallic block a temperature control mechanism, wherein the metallic block possesses exceedingly good heat transfer characteristics so as to become a precisely controlled heat sink for the entire system. All of the significant gaseous passages in the system are confined to flow paths through the heat sink, and therefore a uniform and constant temperature is assured during the measurement process. Water chambers for introducing humidity into the gases are also confined within the heat sink block so as to ensure that humidity is introduced at the same temperature as exists throughout the system. A pair of removable cell covers are clamped against the heat sink, and the necessary flow control and metering valves are all incorporated into the same single metallic block.

It is the principal object of the present invention to provide a gas permeability measurement device having improved temperature control characteristics over the prior art.

It is another object of the present invention to provide a gas permeability measuring device capable of introducing relative humidity into the measurement gas under precise temperature control conditions.

It is another object of the present invention to provide a gas permeability measuring device with a minimum number of connections and fittings in the gas flow paths, to reduce the potential for leakage in the system.

It is a further object of the present invention to provide a gas permeability measuring device having small and compact size for expedient operation.

The foregoing and other objects and advantages of the present invention will become apparent from the following specification and claims, and with reference to the appended drawings.

BRIEF DESCRIPTION OF THE DRAWINGS

FIG. 8 shows a partial cross section of a cell cover;

FIG. 9 shows a cross-section view of a needle valve used in the invention; and

DESCRIPTION OF THE PREFERRED EMBODIMENT

Figure 1:
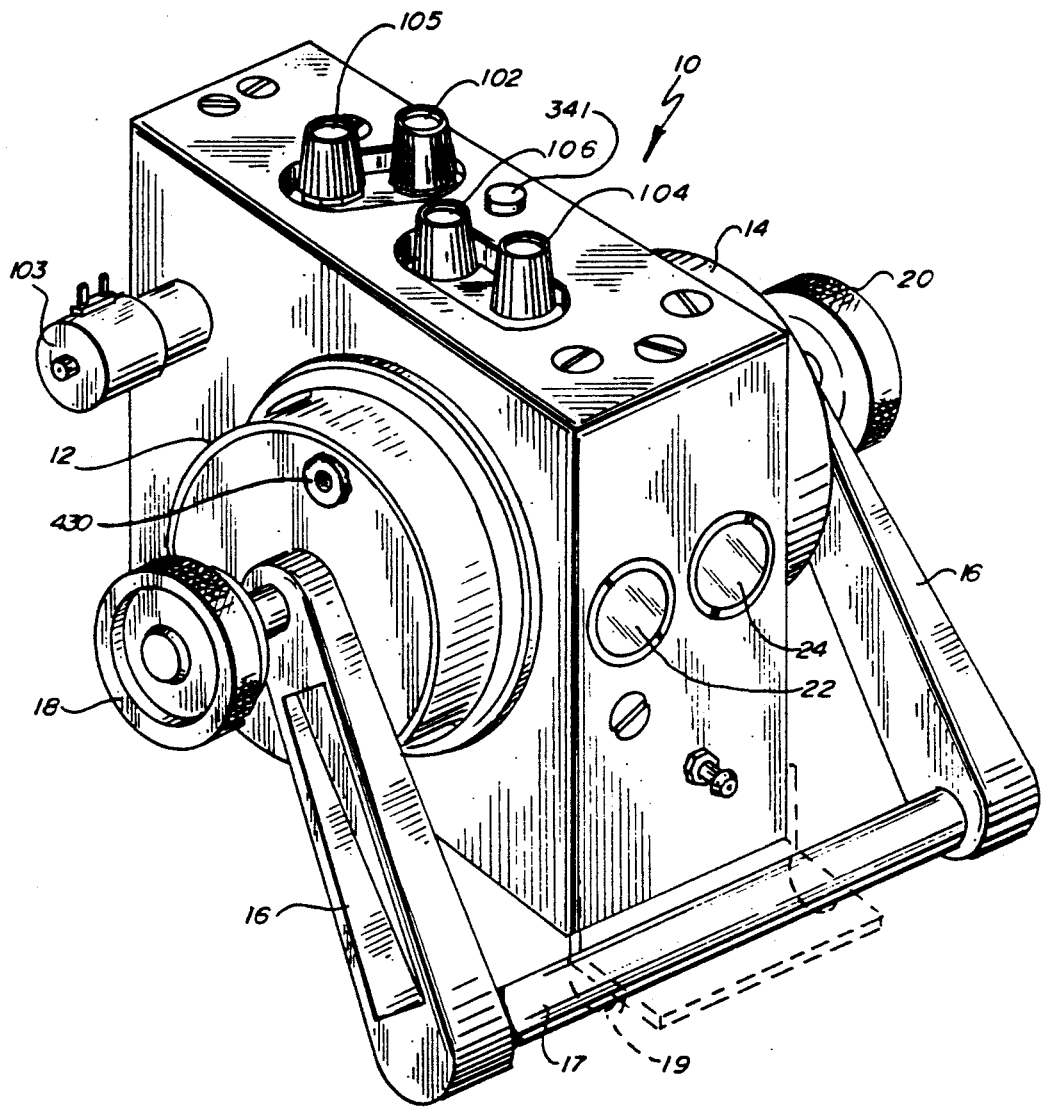
FIG. 1 shows an isometric view of the invention.

Referring first to FIG. 1, there is shown an isometric view of gas permeability detector 10. Permeability detector 10 is adapted for connection to a source of test gas and a source of carrier gas, which in the preferred embodiment are sources of oxygen and nitrogen respectively, and includes two cells for measuring permeability through two different membrane materials. For convenience herein the cells shall be referred to as "test cell A" and "test cell B." Test cell A comprises a chamber which may be subdivided into two halves by means of a test membrane, the chamber being covered by a removable chamber A cover 12. Cover 12 is held securely against the body of permeability detector 10 by means of a lock screw 18. Lock screw 18 is threadably secured into a locking clamp 16, and is threadable through locking clamp 16 to engage against the outer surface of chamber A cover 12. A similar chamber cover 14 exists for chamber B, as does a similar lock screw 20. Locking clamp 16 includes two locking clamp arms rigidly interconnected by a hinge rod 17. Hinge rod 17 is pivotally held within a hinge rod seat 19. Locking clamp 16 may therefore be pivotally swung about the axis of rod 17.

Gas detector 10 has a number of adjustable flow valves associated therewith; flow valve 102 adjustably controls the flow rate of the test gas oxygen through the device, flow valves 104, 105 and 106 adjustably control the flow of the carrier gas nitrogen through various passages in the device. All of the flow valves 104, 105, 106 and 102 are needle valves of a type which will be hereinafter disclosed. In addition to the flow valves described above, the gas detector has a number of solenoid-operated on/off valves, such as valve 103 shown on FIG. 1. Valve 103 may be energized by electrical signals via wires (not shown) to open and close certain flow paths in gas detector 10. Solenoid-operated valves of the type used herein will be described in more detail hereinafter.

The gas detector utilizes a humidifier chamber for each of two gases which may be used with the device; each of the humidifier chambers may be filled with water or other liquid, and the level of such liquid may be monitored via sight glasses sealably installed in the detector. For example, sight glass 22 opens into the humidifier chamber for the nitrogen component, and sight glass 24 opens into the humidifier chamber for the oxygen component.

Figure 2:
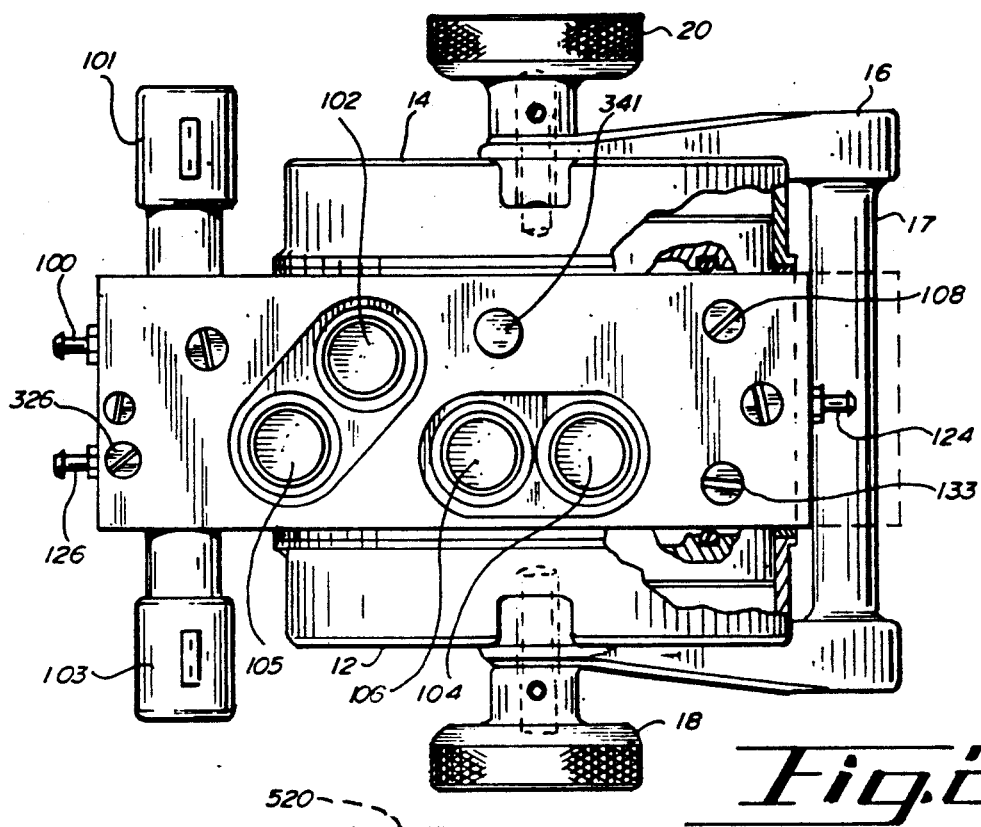
FIG. 2 shows a top view of the invention.

Gas detector 10 has a inlet port 100 for connection to a source of oxygen, and an inlet port 126 for connection to a source of nitrogen (see FIG. 2). Oxygen is exhausted from an exhaust port 124.

Figure 3:
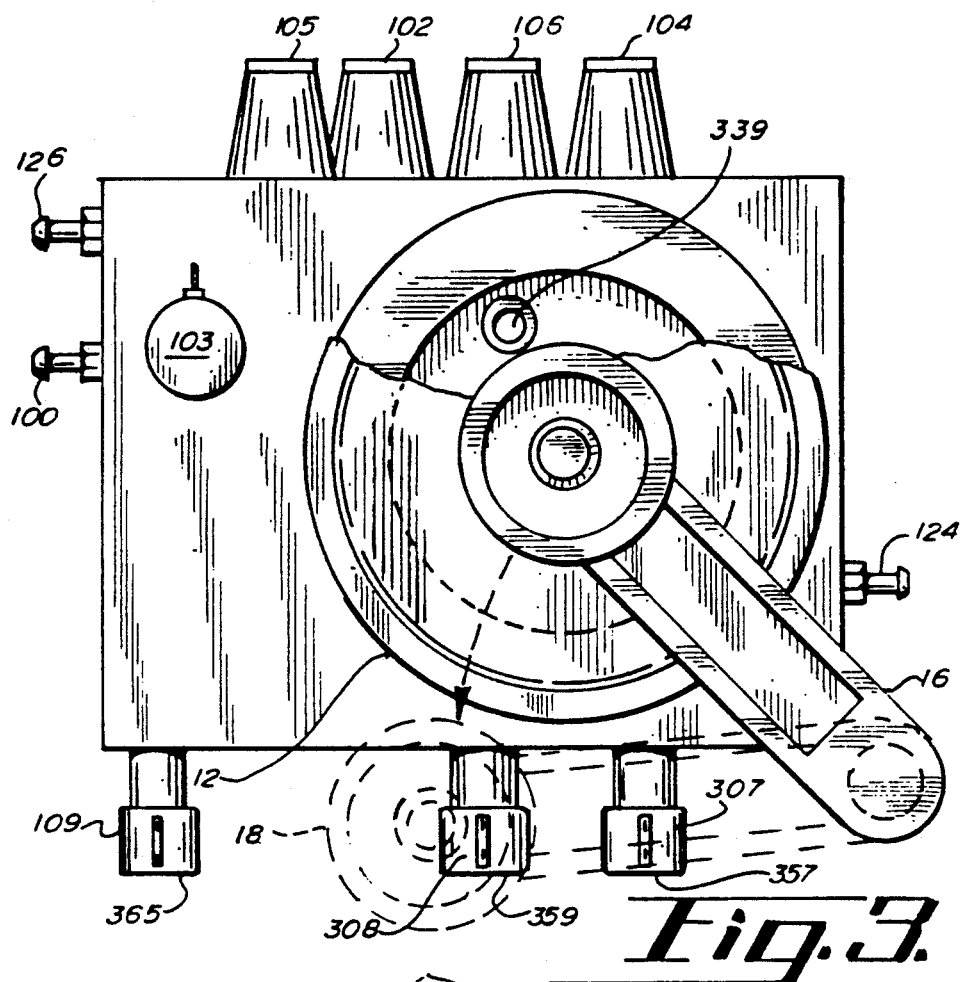
FIG. 3 shows a side elevation view of the invention with the removable cover clamp in two positions.

FIG. 3 shows a side elevational view of gas detector 10, showing locking clamp 16 in solid line in its operable position, clamped against cover 12; and also showing locking clamp 16 in dotted outline in its open position, removed from contact with cover 12. Cover 12 is shown in partial breakaway, to illustrate one of the gas inlet ports into the chamber formed beneath cover 12.

Figure 4:
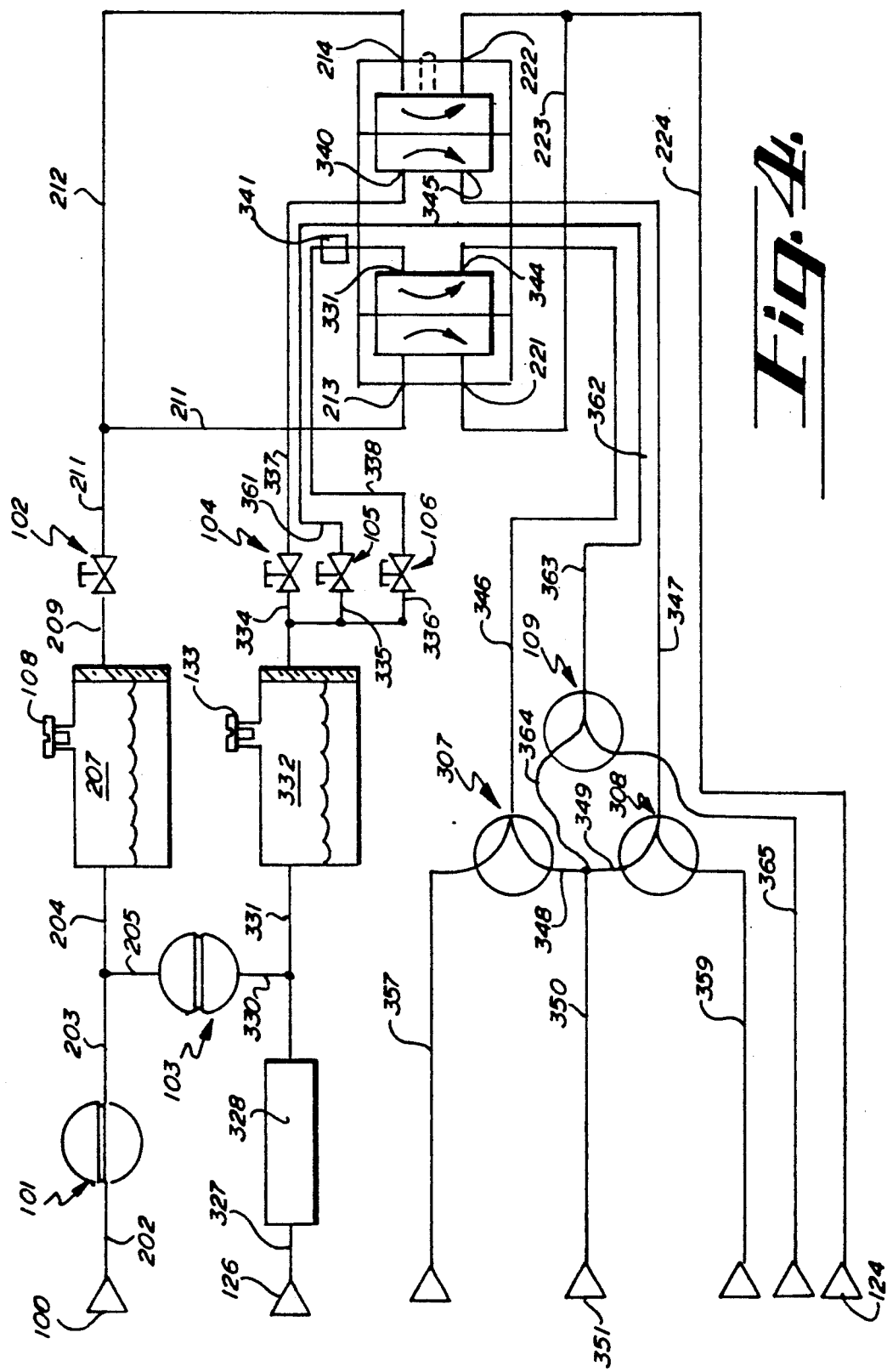
FIG. 4 shows a flow diagram of the invention.

FIG. 4 shows a system flow diagram of the invention, to illustrate the gas flow and operation of the various components. The oxygen inlet 100 is coupled to an oxygen inlet valve 101 which is shown in its normally open position in FIG. 4. The oxygen inlet valve 101 is coupled to a humidifier reservoir 207, and then to the oxygen flow valve 102. Flow valve 102 permits continuous adjustment of the oxygen flow rate through the system. From the oxygen flow valve 102, the oxygen flow paths split to each of the test cells A and B, wherein each test cell has an oxygen inlet port 213, 214, and an oxygen outlet port 221, 222. After the oxygen outlet ports, the two paths are recombined and are coupled to an outlet 124.

The nitrogen flow paths shown in FIG. 4 initiate at nitrogen inlet 126. The nitrogen flow path then proceeds to a catalyst chamber 328, and from there to a humidifier reservoir 332. A nitrogen purge valve 103 is shown in its normally closed position in FIG. 4. The nitrogen flow path from reservoir 332 proceeds through three nitrogen flow control valves. A purge flow control valve 105 is continually adjustable to permit nitrogen to flow through the system to three-way valve 109, where the nitrogen flow may be selectively diverted either to an exhaust outlet line 365 or to an outlet port 351. Outlet port 351 is preferably externally connected to an oxygen sensor or the like, wherein an accurate measurement may be made of oxygen content of the gases passing therethrough. Oxygen sensors of the type described in U.S. Pat. No. 3,223,597, Hersch, may be used with the present invention. Nitrogen flow control valves 104 and 106 are also connected to humidifier reservoir 332, to permit continuous flow adjustment of nitrogen into each of the test cells A and B. In each case, nitrogen flows into a test cell inlet port 339, 340, through the cell and out an exit port 344, 345. For test cell B, the nitrogen outlet is coupled to a three-way flow valve 308, wherein the nitrogen flow may be selectively valved to an exhaust line 359, or to the sensor outlet port 351. Similarly, the nitrogen flow outlet from test cell A is coupled via passages to three-way valve 307, where it may be selectively switched to an exhaust line 357 or to sensor outlet port 351.

Figure 5:
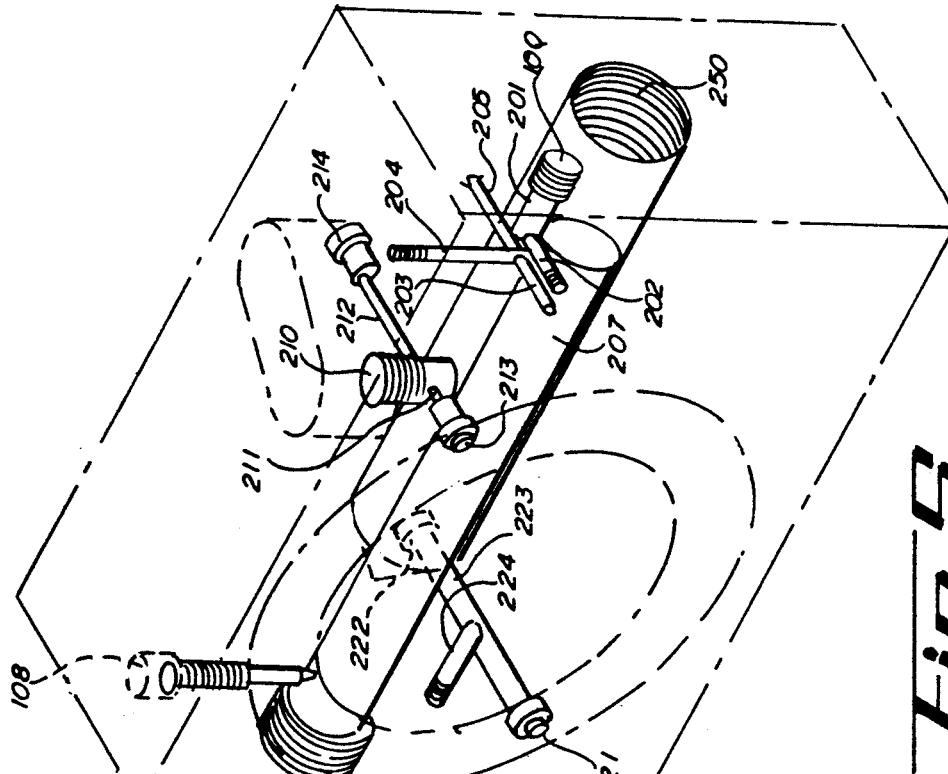
FIG. 5 shows a phantom isometric view illustrating certain gas passages through the invention.

Referring to FIG. 5, the oxygen passages within gas detector 10 are shown in phantom isometric view. Oxygen inlet port 100 is connected at one end of a passage 201 which is drilled to a predetermined depth into detector 10. A passage 202 is cross drilled to intersect passage 201, passage 202 forming one opening into oxygen inlet valve 101. Passage 203 forms the second opening to oxygen inlet valve 101, and a passage 204 is cross drilled to intersect passage 203, and is drilled to a depth sufficient to intersect humidifier passage 207. Passage 204 is plugged at the point where it emerges from the surface of detector body 10. Passage 203 is drilled entirely across the thickness of detector 10, and is denoted as passage 205 to the reverse side of detector 10. Passage 205 forms one inlet to purge valve 103 which will be described hereinafter.

Humidifier passage 207 forms a humidifier reservoir, which may be filled or partially filled with water or other liquid, via a fill port 108. Sight glass 24 (see FIG. 1) permits the operator to view the water level within humidifier passage 207. Oxygen flow valve 102 is threadably secured into passage opening 210, and passage 210 is extended downwardly to intersect humidifier passage 207 via passage 209. A passage 212 is cross drilled to intersect passage 210, passage 212 forming an exit port 213 at one surface of detector 10, and an exit port 214 at the other surface of detector 10. Exit ports 213 and 214 are oxygen inlet ports to the respective chambers A and B, with exit port 213 forming a part of chamber A and port 214 forming a part of chamber B. The respective gas flow exit ports from chambers A and B are ports 221 and 222, which are formed at the ends of a cross-drilled passage 223. A passage 224 is cross drilled to intersect passage 223, and passage 224 is connected to oxygen exhaust port 124 at the surface of detector 10. The foregoing passages represent the oxygen flow passages through gas permeability detector 10.

An enlarged passage 250 opens through an end surface of detector 10, and extends to a depth of approximately two-thirds of the length of detector 10. Passage 250 may be used to insert a temperature control device into the interior of detector 10, for the purpose of stabilizing the temperature of detector 10 at any predetermined temperature. For example, an electrical heating element may be inserted into passage 250 for the purpose of elevating the temperature to a predetermined temperature above ambient. As a further example, a flow of liquid at any predetermined temperature may be circulated through passage 250, for purposes of either heating or cooling. Because the entire detector 10 is made from a single metallic block, it is relatively easy to stabilize the temperature of the entire block, and therefore all of the internal passageways, through the use of heating and/or cooling media in passage 250.

Figure 7:
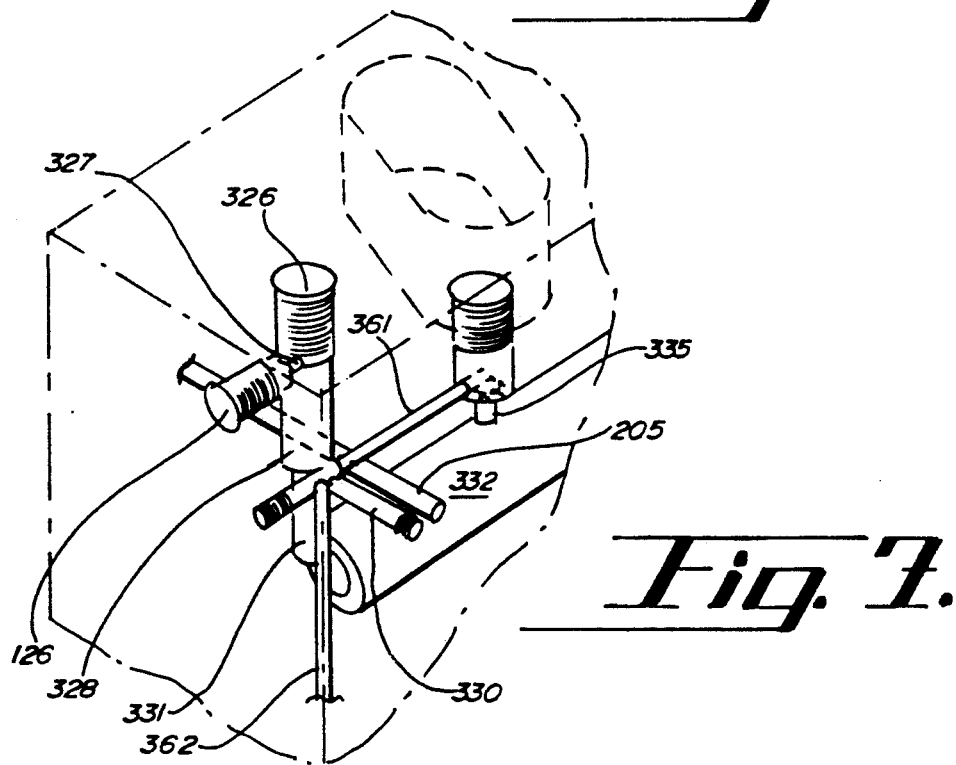
FIG. 7 shows an exploded partial phantom isometric view of a portion of FIG. 6.
Figure 6:
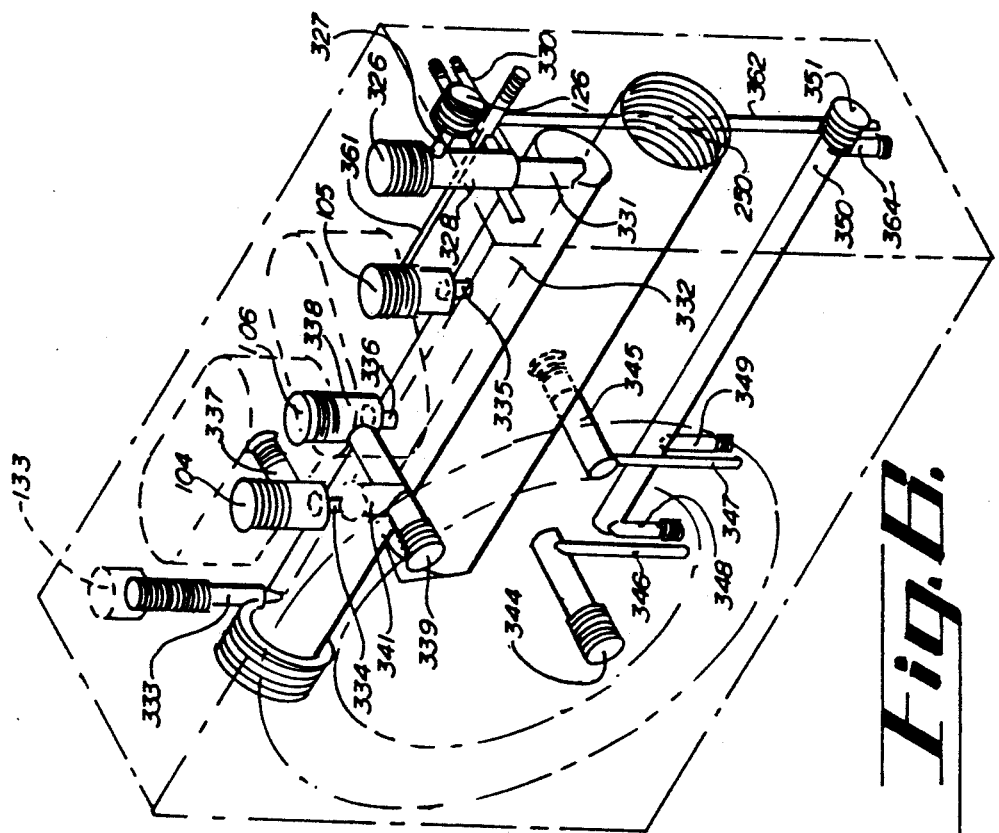
FIG. 6 shows a further phantom isometric view showing further gas passages through the invention.

FIGS. 6 and 7 show the nitrogen flow passages in gas detector 10, in phantom isometric view. A nitrogen inlet port 126 is connected to a passage 327, which is cross drilled into a larger passage 328. The larger passage may have a catalyst material inserted therein, and passage 328 is enclosed by means of a removable plug 326. The catalyst material may be a type which will remove contaminants from the carrier gas flow. Passage 328 has a lower extended passage 331 which intersects and opens into humidifier passage 332. Humidifier passage 332 forms a humidifier reservoir, which may be filled or partially filled with water or other liquid via a fill port 133. A sight glass 22 (see FIG. 1) permits the operator to view the liquid level within humidifier passage 332.

A small passage 330 is cross drilled into passage 328, and passage 330 opens to the rear surface of detector 10. A two-way purge valve 103 is affixed to the outer surface of detector 10 at the opening of passage 330, to provide a controllable flow path between passage 330 and passage 205. Passage 205 opens into the oxygen passages described hereinbefore. A passage 335 is drilled to open into humidifier passage 332, passage 335 also opening into an enlarged opening for placement of a purge flow valve 105. A second passage 361 is cross drilled into the enlarged opening adjacent passage 335, and the flow path between the passages 361 and 335 is controlled by purge flow valve 105. A passage 362 is cross drilled to intersect with passage 361, passage 362 being brought to the lower surface of detector 10, closely adjacent to parallel passage 364. A three-way purge selection valve 109 is affixed at the exterior opening of passages 362 and 364, to regulate the flow therebetween. Passage 364 is cross drilled to open into passage 350, which opens through the side surface of detector 10 at port 351. A suitable connector may be threadably secured to port 351, to connect to an external oxygen sensor.

A further passage 349 is cross drilled to open into passage 350, and is opened through the lower surface of detector 10, closely adjacent a parallel passage 347. A three-way valve 308 is affixed to the lower surface of detector 10, to regulate the flow path between passages 347 and 349. Passage 347 is cross drilled to open into a passage 345, and passage 345 opens into the B cell on the side of detector 10. A passage 348 also opens into passage 350, and is opened to the lower surface of detector 10, closely spaced with passage 346. A three-way valve 107 is affixed to the lower surface to regulate the flow between passages 346 and 348. Passage 346 also opens into a passage 344, which itself opens into the A cell chamber. A second passage opening into the A cell chamber is passage 339, which is also drilled to intersect with an enlarged passage 338. Passage 338 is drilled sufficiently deep to open into humidifier passage 332, and the top opening of passage 338 is sized to accommodate a nitrogen flow valve 106. A further passage 341 is cross drilled to intersect passage 339, and opens through the top surface of detector 10. A removable plug is sealably inserted into passage 341 for purposes to be hereinafter described.

A further passage 334 is cross drilled downwardly to open into humidifier passage 332, and a passage 337 is cross drilled from the side surface into passage 334. Passage 337 opens into the cell B chamber. The enlarged top opening of passage 334 is sized to accept a nitrogen flow valve 104, to regulate the flow rate of nitrogen into cell B. Finally, a passage 333 is cross drilled to open into humidifier passage 332, passage 333 having a removable top plug to permit the filling of fill part 133 with water or other liquid.

Referring to FIG. 7, some of the nitrogen flow passages are shown in exploded view. Passage 362 is cross drilled from below to open into passage 361, and passage 361 opens into passage 335. Passage 335 has a lower opening into humidifier passage 332, and has an upper opening through the top surface of detector 10 which is sized to accommodate the purge flow valve 105. Passage 205 and 330 are brought out through the side surface of detector 10, and the flow between these passages is regulated by a two-way nitrogen purge valve 103.

FIG. 8 shows a side cross-section view of the elements which form the test chamber. For ease of illustration, the inlet and outlet ports into the chamber have been rotated in this cross-section view so as to appear along a common plane; it is understood that in the actual unit the inlet and outlet ports may be positioned along different intersecting planes of the chamber. A clamping force indicated by arrow 120 is applied against cover 12, by the combined effect of locking clamp 16 and lock screw 18. This clamping force securely holds cover 12 against the body of detector 10, and clamps an intermediate test membrane 122 between cover 120 and the body of detector 10. Membrane 122 may be formed of a thin plastic film or other similar material, to form a barrier between a cover chamber 402 and a body chamber 404. An O-ring 400 is seated about the periphery of the chambers formed thereby, so as to provide a sealed enclosure.

An oxygen inlet port 213 is formed by a hollow pin 406 which is affixed in cover 12. Hollow pin 406 is insertable into a corresponding opening in the body of detector 10, and an O-ring 407 assures a tight gas seal. A passage 408 is cross drilled in cover 12 to intersect inlet passage 213, and a second passage 410 is cross drilled to intersect passage 408. Passage 408 opens into chamber 402 to permit the flow of oxygen into chamber 402. An oxygen outlet 221 is formed by a similar hollow pin 416 affixed to cover 12, and a passage 418 is cross drilled to intersect passage 221. A small passage 420 is cross drilled to intersect passage 418, and thereby to provide an opening into chamber 402. Oxygen flows through the chamber 402 and out the outlet port 221, whereby hollow pin 416 is sealably coupled to the body of detector 10 by means of an O-ring 417.

A nitrogen inlet passage 339 opens into chamber 404, and a nitrogen outlet passage 344 also opens into chamber 404. Nitrogen is therefore permitted to flow into chamber 404 via inlet 339 and out of chamber 404 via outlet 344. The outer ends of passages 408 and 418 are plugged as illustrated in FIG. 8. A port 430 is shown in dotted outline in FIG. 8, which port may be closed by a removable plug. The purpose of port 430 is to permit the insertion of a relative humidity probe into the oxygen chamber 402, so that external measurements may be made to determine the relative humidity within chamber 402.

FIG. 9 shows a cross-sectional view of a typical flow valve, for example flow valve 102. Flow valves 102, 104, 105 and 106 are all made according to the illustration of FIG. 9, and are commercially available flow valves. One commercially available valve which may be used in connection with this invention is a valve designated as a flow control valve No. 5947L001GEA, manufactured by Brooks Instrument Division, Emerson Electric Company, Hatfield, Pa. Flow valve 102 has an inlet port 209 which is sealably blocked by a portion of the valve body 501, in cooperation with O-ring 502. A retractable valve body portion 503 is connected to valve knob 504. Valve knob 504, and retractable portion 503, may be threadably inserted into or retracted out of the valve, thereby inserting and/or withdrawing a tapered needle 506 into a port 507. As the needle is threadably retracted from the port 507 an increasing gap appears between the needle and the port, thereby providing a flow communication path from inlet 209 to outlet 211. The flow rate passing through the valve may thereby be controlled by selective adjustment of the valve.

Figure 10:
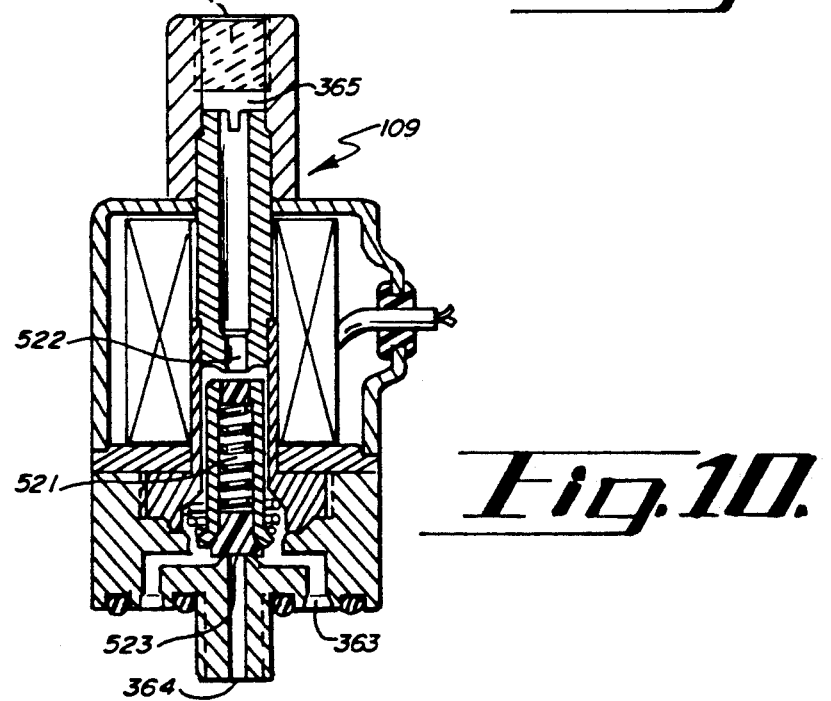
FIG. 10 shows a cross-section view of a solenoid valve used in the invention.

FIG. 10 shows an illustration of a typical two-way or three-way solenoid valve as used with the present invention. These valves are also commercially available, from Precision Dynamics, Inc., of New Britain, Conn. The two-way solenoid valve is available under Type Designation G-2014-MM-512, and the three-way solenoid valve is available under Type Designation G-3114-MM-S7. In both cases, the overall valve construction is very similar. For example, referring to FIG. 10, an upper plug 520 is shown in dotted outline, threadably secured to block a passage through the top of the valve. In the case of a two-way solenoid valve, plug 520 is inserted as shown in FIG. 10; in the case of three-way valve, plug 520 is omitted from the construction. Referring to purge selection valve 109 by way of example, there is an annular inlet port 363 which may communicate with either an outlet port 364 or an outlet port 365. When the solenoid is energized, the slidable valve section 521 moves upwardly to block opening 522, and to unblock opening 523. In this position, inlet port 363 is in flow communication with outlet port 364. If the solenoid valve is deenergized slidable element 521 moves downwardly to block inlet opening 523 into open inlet 522. This permits flow communication between inlet port 363 and outlet port 365.

In the present invention, oxygen inlet valve 101 and purge valve 103 are each two-way solenoid valves; purge selection valve 109, and nitrogen selection valves 307 and 308 are each three-way solenoid valves.

In operation, a film membrane which is to undergo tests is mounted into each of the chambers A and B, by inserting a section of the film membrane between a cover and the body of detector 10. The respective lock screws are tightened to fully compress the cover and film membrane against the body of detector 10, thereby to assure a leak-free connection. The oxygen inlet valve is shut off, all of the solenoid valves are deenergized, and the nitrogen purge valve is turned on, thereby to permit nitrogen to flow through the passages of the system to purge undesirable gases from the system. At the same time, the flow control valves may be adjusted to accommodate the desired flow rate of gases through the system during a test procedure. If desired, a suitable temperature medium is introduced into the temperature control passage 250, until the system temperature has stabilized at some preselected temperature value.

When a desired test procedure is undertaken, the nitrogen purge valve is first shut off and the oxygen inlet valve is turned on, to permit the flow of oxygen into the two test cells on one side of each of the film membrane barriers. A flow of nitrogen may be maintained through the test cells on the other side of the film membranes, and one or more of the selection valves may be activated to permit gas flow from either of the test cells to pass to a gas sensor device connected to outlet port 351. The measurements made by the gas sensor device are recorded and maintained over predetermined time, thereby to provide a measure of oxygen permeability of the respective test membranes under the predetermined test conditions.

The test procedure may be performed under controlled relative humidity conditions by use of the respective humidity reservoirs, and a nitrogen relative humidity measurement may be made via a relative humidity sensor connected at an inlet port coupling 341. An oxygen relative humidity measurement may be made via a relative humidity sensor connected at inlet port 430. Relative humidity calculations may be made by the two-pressure method. The inlet pressures of both the test gas and the carrier gas is controlled by a pressure regulator (not shown), at some pressure elevated above atmospheric pressure. Therefore, the elevated pressure in humidifiers 207 and 332 exceeds atmospheric pressure, and the relative humidity in each of these humidifiers is 100% RH. The relative humidity at any point subsequent to the humidifiers is directly proportional to the pressure drop at that point. For example, if a gas is at 100% RH at a pressure of 30 psia, and the gas is exhausted to ambient pressure (15 psia), the relative humidity of the exhaust gas is 50% RH.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. Apparatus for measuring gas permeability of a membrane material, comprising:
   a. a material volume formed of a solid metal block having high thermal conductivity characteristics so as to maintain a substantially uniform temperature throughout all regions of its volume;
   b. at least one first cavity formed on an exterior surface of said material volume, said at least one first cavity being surrounded by a peripheral flat surface formed on said exterior surface;
   c. at least one removable cover sealably affixable against said peripheral flat surface, said at least one cover having a second cavity which is alignable with said at least one first cavity, including means for clamping said membrane material between said cavities;
   d. a plurality of passages formed in said material volume and said removable cover, including
      i) a first set of passages in the interior of said material volume, having a first opening through a surface of said material volume, and a second opening into one of said first cavities, and means for connecting said first opening to a first source of gas;
      ii) a second set of passages in the interior of said material volume, having a first opening through a surface of said material volume, and a second opening into said second cavity, and means for connecting said first opening to a second source of gas;
      iii) a third set of passages in the interior of said material volume, having a first opening into one of said first cavities, and a second opening through a surface of said material volume;
      iv) a fourth set of passages in the interior of said material volume, having a first opening into said second cavity, and a second opening through a surface of said material volume;
   e. means for connecting a gas detector to one of said second openings of said third set of passages or said fourth set of passages;
   f. a fifth set of passages in the interior of said material volume, said fifth set of passages having a first and second opening through a surface of said material volume; and
   g. means for connecting the first and second openings of said fifth set of passages to a source of heat transfer liquid whereby the heat transfer liquid passing through said fifth set of passages determines the temperature of the entire material volume and passages therein.

2. The apparatus of claim 1, further comprising a first valve attached to said material volume, said first valve having a gas flow regulating member extending into said first set of passages, thereby to control the gas flow rate therethrough.

3. The apparatus of claim 2, further comprising an enlarged passage section entirely within the interior of said material volume, comprising a portion of said first set of passages, said enlarged section formed into a liquid reservoir; and a liquid fill passage extending from said enlarged section to the surface of said material volume.

4. The apparatus of claim 3, further comprising a second valve attached to said material volume; and branching passages between said first set of passages and said second set of passages; said second valve having a passage closure member extending into said branching passages, thereby to open and close said branching passages.

5. The apparatus of claim 4, further comprising means for measuring the relative humidity in at least one of said cavities.

6. The apparatus of claim 5, wherein said material volume further comprises a unitary structure made from a metal.

7. The apparatus of claim 6, wherein said metal further comprises aluminum.

8. The apparatus of claim 7, wherein said first source of gas further comprises a source of oxygen.

9. The apparatus of claim 8, wherein said second source of gas further comprises a source of nitrogen.

10. An apparatus for measuring gas permeability of a membrane material under controlled humidity conditions, comprising:
    a. a material volume formed of a solid metal block having good thermal conductivity characteristics so as to maintain a substantially uniform temperature throughout all regions of said volume;
    b. a plurality of gas-conveying passages in the interior of said material volume, including at least one enlarged chamber formed wholly within the interior of said material volume in at least one of said passages, and a fill passage extending from said at least one enlarged chamber to the surface of said material volume; and
    c. a plurality of further passages in the interior of said material volume, said further passages coupled to a first and second opening through the surface of said material volume, and means for connecting a source of heat transfer liquid to said first and second openings, and means for circulating said heat transfer liquid through said further passages, whereby to control the temperature of said material volume.

11. The apparatus of claim 10, further comprising a first enlarged recess in the exterior surface of said material volume, at least two of said plurality of gas-conveying passages opening into said first enlarged recess; a further material volume having a further enlarged recess in one surface thereof; means for aligning said further enlarged recess with said first enlarged recess and means for clamping said further material volume against said material volume with said respective enlarged recesses in alignment; and means for connecting at least two further of said plurality of gas-conveying passages into said further enlarged recess.

* * * * *